United States Patent
Ogura et al.

(10) Patent No.: US 9,570,264 B2
(45) Date of Patent: Feb. 14, 2017

(54) X-RAY GENERATOR AND X-RAY IMAGING APPARATUS

(75) Inventors: Takao Ogura, Yokohama (JP); Yasue Sato, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 324 days.

(21) Appl. No.: 14/241,417

(22) PCT Filed: Aug. 29, 2012

(86) PCT No.: PCT/JP2012/072515
§ 371 (c)(1),
(2), (4) Date: Feb. 26, 2014

(87) PCT Pub. No.: WO2013/032015
PCT Pub. Date: Mar. 7, 2013

(65) Prior Publication Data
US 2014/0211919 A1 Jul. 31, 2014

(30) Foreign Application Priority Data

Aug. 31, 2011 (JP) ................................. 2011-189111

(51) Int. Cl.
*H01J 35/02* (2006.01)
*H01J 35/08* (2006.01)
(Continued)

(52) U.S. Cl.
CPC ............... *H01J 35/02* (2013.01); *G01N 23/04* (2013.01); *H01J 35/08* (2013.01); *H01J 35/14* (2013.01);
(Continued)

(58) Field of Classification Search
CPC ..................... H01J 2235/087; H01J 2235/186; H01J 35/32; H01J 35/14; H01J 35/02; H01J 35/08; G01N 23/04
(Continued)

(56) References Cited

U.S. PATENT DOCUMENTS 3,840,748 A * 10/1974 Braunlich ............... H01J 27/26
250/423 R
4,159,437 A * 6/1979 Sahores .................. H01J 35/18
378/140
(Continued)

FOREIGN PATENT DOCUMENTS

CN 1252618 A 5/2000
CN 1971834 A 5/2007
(Continued)

OTHER PUBLICATIONS

Filter Transmission, Dec. 6, 2012, Retrieved from the Internet: URL: http: //henke.1b1.gov/optical_constants/filter2.html.
(Continued)

*Primary Examiner* — Wyatt Stoffa
(74) *Attorney, Agent, or Firm* — Canon USA, Inc. I.P. Division

(57) ABSTRACT

Provided is an X-ray generator which includes:
an electron path 8; a target 9c disposed on a substrate 9a, in which electrons having passed through the electron path 8 are made to emit at the target 9c and to generate an X-ray, wherein: the target 9c is disposed at the central area of the substrate 9a; at least a part of a peripheral area of the substrate 9a which is not covered with the target 9c has higher transmittance than that of the central area of the substrate 9a covered with the target 9c, with respect to the X-ray generated when electrons having reflected from the target enter an inner wall of the electron path. X-ray generation efficiency may be improved by effectively using electrons reflected off the target 9c.

10 Claims, 10 Drawing Sheets

(51) Int. Cl.
*G01N 23/04* (2006.01)
*H01J 35/14* (2006.01)

(52) U.S. Cl.
CPC ..... *H01J 2235/087* (2013.01); *H01J 2235/186* (2013.01)

(58) Field of Classification Search
USPC .......................................................... 378/62
See application file for complete search history.

(56) References Cited

U.S. PATENT DOCUMENTS

| | | | |
|---|---|---|---|
| 6,151,384 A | 11/2000 | Reed et al. | |
| 6,252,936 B1* | 6/2001 | Smit | H01J 35/08 378/141 |
| 6,661,876 B2* | 12/2003 | Turner | G01N 23/223 313/553 |
| 7,130,379 B2* | 10/2006 | Hamann | H01J 35/08 378/119 |
| 7,233,647 B2* | 6/2007 | Turner | G21K 1/10 378/140 |
| 7,382,862 B2* | 6/2008 | Bard | H01J 35/14 378/121 |
| 7,783,011 B2* | 8/2010 | Ito | H01J 9/26 378/121 |
| 2003/0021377 A1* | 1/2003 | Turner | G01N 23/223 378/102 |
| 2004/0076260 A1* | 4/2004 | Charles, Jr. | H01J 35/08 378/124 |
| 2005/0207537 A1* | 9/2005 | Ukita | H01J 35/28 378/125 |
| 2005/0276382 A1 | 12/2005 | Lesiak et al. | |
| 2007/0076849 A1* | 4/2007 | Bard | H01J 35/14 378/121 |
| 2009/0028297 A1* | 1/2009 | Matoba | H01J 35/08 378/140 |
| 2009/0041196 A1 | 2/2009 | Matoba | |
| 2009/0279669 A1 | 11/2009 | Allen et al. | |
| 2011/0058655 A1* | 3/2011 | Okumura | H01J 35/12 378/143 |
| 2011/0085641 A1* | 4/2011 | Okunuki | H01J 35/065 378/62 |
| 2012/0140895 A1* | 6/2012 | Okunuki | H01J 35/065 378/122 |
| 2012/0318987 A1* | 12/2012 | Miyazaki | H01J 35/08 250/358.1 |
| 2014/0211919 A1* | 7/2014 | Ogura | H01J 35/08 378/62 |
| 2014/0362972 A1* | 12/2014 | Ogura | H01J 35/14 378/62 |
| 2014/0362973 A1* | 12/2014 | Ogura | H01J 35/08 378/62 |
| 2014/0369469 A1* | 12/2014 | Ogura | H01J 35/08 378/62 |
| 2015/0117616 A1* | 4/2015 | Ishii | H01J 35/08 378/137 |

FOREIGN PATENT DOCUMENTS

| | | |
|---|---|---|
| CN | 101355002 A | 1/2009 |
| EP | 777255 A1 | 6/1997 |
| EP | 2293318 A1 | 3/2011 |
| GB | 2473137 A | 3/2011 |
| JP | 2-297850 A | 12/1990 |
| JP | 9-171788 A | 6/1997 |
| JP | H11-144653 A | 5/1999 |
| JP | 2002-352754 A | 12/2002 |
| JP | 2005-523558 | 8/2005 |
| JP | 2006-236656 A | 9/2006 |
| JP | 2009-031167 A | 2/2009 |
| JP | 2009-031168 A | 2/2009 |
| JP | 2009-189507 A | 8/2009 |
| JP | 2009-205992 | 9/2009 |
| JP | 2010027302 A | 2/2010 |
| JP | 2011-071101 A | 4/2011 |
| JP | 2011-077027 A | 4/2011 |
| WO | 2007/100105 A1 | 9/2007 |
| WO | 2008/156361 A2 | 12/2008 |
| WO | 2011/105035 A2 | 9/2011 |

OTHER PUBLICATIONS

Jensen, et al, "Improvements in Low Power, End-Window, Transmission-Target X-Ray Tubes", vol. 47, 2004, pp. 64-69. (the year of publication for this reference is sufficiently earlier than the effective U.S. filing late and any foreign priority date so that the particular month of publication is not in issue.).

Cornaby, et al, "Simultaneous XRD/XRF With Low-Power X-Ray Tubes", vol. 45, Jan. 1, 2002, pp. 34-40.

International Search Report and Written Opinion for PCT/JP2012/072514 and notification of transmittal of the ISR/WO, lated Dec. 10, 2012.

International Search Report and Written Opinion for PCT/JP2012/072524 and notification of transmittal of the ISR/WO, lated Apr. 18, 2013.

International Search Report and Written Opinion for PCT/JP2012/072522 and notification of transmittal of the ISR/WO, lated Dec. 12, 2012.

* cited by examiner

X-RAY GENERATOR AND X-RAY IMAGING APPARATUS

TECHNICAL FIELD

The present invention relates to a transmission type X-ray generator applicable to radiography for diagnosis in the medical field, a non-destructive test in the industrial machinery field and other use. The present invention also relates to X-ray imaging apparatus to which the transmission type X-ray generator is applied.

BACKGROUND ART

Generally, in a transmission type X-ray generator which emits electrons at a transmission target and makes an X-ray be generated, X-ray generation efficiency is significantly low. When electrons are accelerated to high energy and emitted at the transmission target to make an X-ray be generated, the ratio of energy of electrons that becomes the X-ray is only 1% or less of the entire electrons colliding with the transmission target: the rest, about 99% or more, of the electrons becomes heat. Therefore, improvement in X-ray generation efficiency is required. When the electrons collide with the transmission target, reflected electrons are generated. It is known that the reflected electrons do not contribute to generation of the X-ray.

PTL 1 discloses an X-ray tube with improved X-ray generation efficiency. X-ray generation efficiency is improved in the following manner: an anode member provided with a conical channel of which opening diameter is reduced from an electron source toward a target is disposed between the electron source and the target; and electrons are made to be elastically scattered on a channel surface and enter the target.

PTL 2 discloses a transmission X-ray target in which target metal is formed on a ceramic or glass X-ray transmission window substrate.

CITATION LIST

Patent Literature

PTL 1 Japanese Patent Laid-Open No. 9-171788
PTL 2 Japanese Patent Laid-Open No. 2002-352754

SUMMARY OF INVENTION

Technical Problem

The technique described in PTL 1 provides a microfocus X-ray tube having a substantially increased number of electrons entering the target. However, this technique is not necessarily sufficient in X-ray generation efficiency of the X-ray tube for the use as an X-ray imaging apparatus. The technique described in PTL 2 may prevent charge-up of the target but not improve X-ray generation efficiency.

Solution to Problem

An X-ray generator according to the present invention includes an electron path formed by an electron path formation member which surrounds a periphery of the electron path; and a target disposed on an insulating substrate, in which electrons having passed through the electron path are made to be emitted at the target and to generate an X-ray, wherein: the target is disposed at the central area of the substrate; at least a part of a peripheral area of the substrate which is not covered with the target has higher transmittance than that of the central area of the substrate covered with the target, with respect to the X-ray generated when electrons reflected from the target are irradiated to an inner wall of the electron path.

Advantageous Effects of Invention

According to the present invention, besides the X-ray generated at the transmission target, the X-ray generated from reflected electrons generated at the transmission target may be taken out efficiently. Therefore, X-ray generation efficiency may be improved and a high-output transmission type X-ray generator suited for radiography may be provided.

DESCRIPTION OF EMBODIMENTS

A target area 9 of the present invention consists of a target support base (hereafter, "substrate") 9a and a transmission target (hereafter, "target") 9c disposed on the substrate.

First Embodiment

Figure 1A:
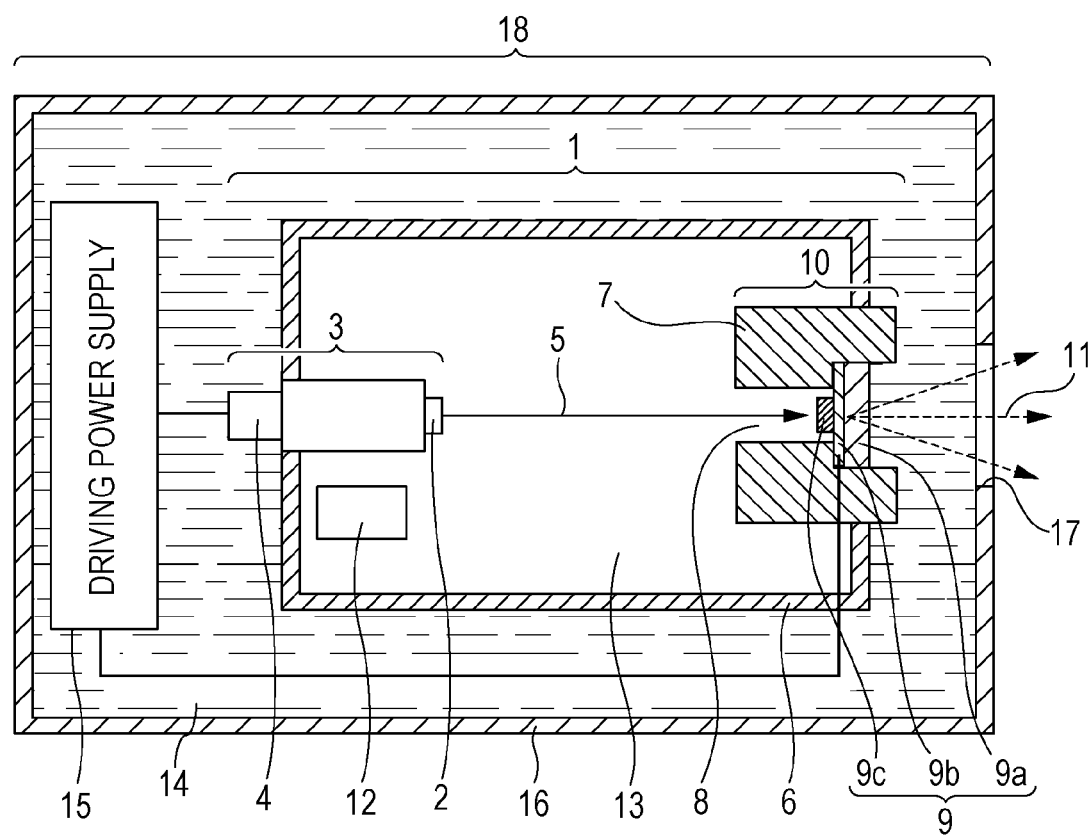
FIG. 1A is a schematic diagram of a configuration of an X-ray generator according to a first embodiment of the present embodiment.
Figure 1B:
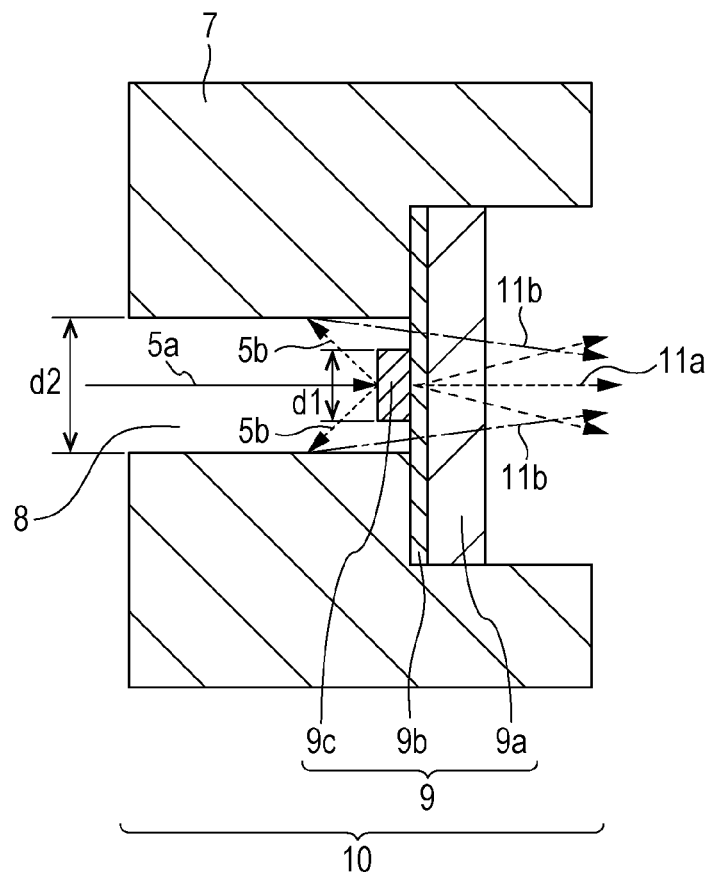
FIG. 1B is a schematic diagram of a configuration of an anode which constitutes the X-ray generator.
Figure 1C:
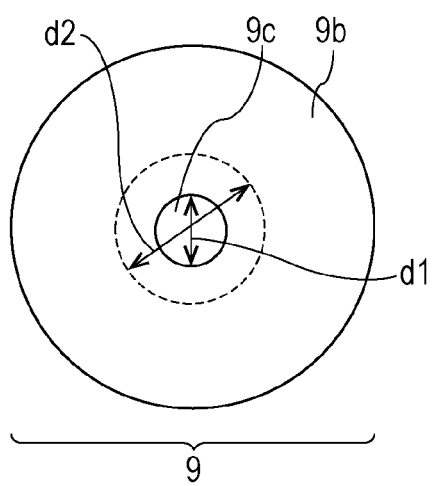
FIG. 1C is a schematic diagram of a configuration of a target area which constitutes the X-ray generator.

FIG. 1A is a cross-sectional view of an exemplary configuration of a transmission type X-ray generator (hereafter, "X-ray generator") 18 according to the present embodiment. FIG. 1B is an enlarged cross-sectional view of an anode 10 illustrated in FIG. 1A. FIG. 1C is a plan view of a target area 9 illustrated in FIG. 1A seen from the target side.

The X-ray generator 18 consists of an X-ray source 1 and a driving power source 15 which are disposed in an envelope 16, and insulation oil 14 with which ullage space in the envelope 16 is filled. The envelope 16 is provided with an X-ray extraction window 17.

The X-ray source 1 consists of an electron source 3, an anode 10, a getter 12 and a vacuum vessel 6.

The electron source 3 consists of a current introducing terminal 4 and an electron emitting portion 2. A mechanism of the electron source 3 for emitting electrons may be any electron source capable of controlling the amount of electrons emitted from outside the vacuum vessel 6. For example, a hot cathode electron source and a cold cathode electron source may be used. The electron source 3 is electrically connected to a driving power source 15 disposed outside the vacuum vessel 6 so as to be capable of controlling the amount of electrons emitted and ON and OFF states of the electron emission via the current introducing terminal 4 disposed to penetrate the vacuum vessel 6.

The electrons emitted from the electron emitting portion 2 become an electron beam 5 having energy of about 10 keV to 200 keV via an unillustrated extraction grid and an unillustrated accelerating electrode. The electron beam 5 is capable of entering a target 9c disposed to face the electron emitting portion 2. The extraction grid and the accelerating electrode may also be incorporated in a hot cathode electron gun tube. The extraction grid and the accelerating electrode may also be connected to an external unillustrated correction circuit in a state in which a correction electrode for adjustment of irradiation spot position of the electron beam and astigmatic adjustment of the electron beam is added to the electron source 3.

The anode 10 is constituted by a substrate 9a, a conductive layer 9b, the target 9c and an electron path formation member 7. The substrate 9a functions also as an X-ray transmission window.

It is necessary that the substrate 9a is high in radiolucency, high in heat conduction, and highly durable to vacuum lock. For example, the substrate 9a may be made of diamond, silicon nitride, silicon carbide, aluminum carbide, aluminum nitride, graphite and beryllium. Diamond, aluminum nitride and silicon nitride are particularly desirable because these materials are lower in radiolucency than aluminum and higher in thermal conductivity than tungsten. Insulative materials may also be used. The thickness of the substrate 9a may be determined arbitrarily as long as the function described above is carried out: desirably, 0.3 mm or more to 2 mm or less depending on the material. Among these, diamond is more suitable for its high thermal conductivity, high radiolucency, and high capability of keeping the vacuum state. These materials decrease significantly in thermal conductivity as temperature rises: therefore, it is necessary to control temperature of the substrate 9a rise as much as possible.

The conductive layer 9b is provided for the purpose of preventing charge-up of the target area 9 by the electrons when the target 9c is irradiated with the electron beam 5. Therefore, the conductive layer 9b may be made of any conductive material including many kinds of metallic materials, carbide and oxide. The conductive layer 9b may be integrated with the substrate 9a by sputtering, vapor deposition, or other methods. If the substrate 9a is a conductive material, such as graphite and beryllium, or an insulating material capable of being provided with electrical conductivity by additives, it is not necessary to provide the conductive layer 9b. However, commercially available insulating materials, such as diamond, generally have no electrical conductivity, and therefore it is necessary to provide the conductive layer 9b. If the conductive layer 9b is provided, it is possible to supply voltage to the target 9c via the conductive layer 9b.

If the conductive layer 9b is provided only for the purpose of preventing charge-up of the target area 9, the conductive layer 9b may be any materials of any thickness as long as they have electrical conductivity. In the present invention, however, it is intended that the conductive layer 9b has a function to extract the X-ray generated at an inner wall surface of the electron path 8 formed by the electron path formation member 7: therefore, the type and thickness of the material of the conductive layer 9b is important. Generation of the X-ray on the inner wall surface of the electron path 8, a method for extracting the X-ray, and the material and type of the conductive layer 9b will be described later.

Typically, the target 9c may be made of a metallic material of atomic number 26 or larger. Materials having greater thermal conductivity and higher melting point are more suitable. Namely, metallic materials, such as tungsten, molybdenum, chromium, copper, cobalt, iron, rhodium and rhenium, or alloys thereof may be used suitably. The thickness of the target 9c is 1 μm to 15 μm although the optimum value of the thickness depends on the acceleration voltage which affects transmission depth of the electron beam to the target 9c, i.e., an area in which the X-ray is generated. The target 9c may be integrated with the conductive layer 9b by sputtering, vapor deposition, or other methods. In a configuration in which no conductive layer 9b is provided, the target 9c may also be integrated with the substrate 9a by sputtering, vapor deposition, or other methods. Another method for integration includes fabricating a thin layer of the target 9c of predetermined thickness by rolling or polishing, and then carrying out diffusion bonding to the substrate 9a under high temperature and high pressure.

The electron path formation member 7 is provided with an electron path 8 which opens at both ends. Electrons enter from one end of the electron path 8 (i.e., an opening at the electron source 3 side) and the target 9c provided at the other end of the electron path 8 (i.e., at the side opposite to the electron source 3) is irradiated with the electrons, whereby an X-ray is generated. The electron path 8 functions as a path for guiding the electron beam 5 to an electron beam irradiation region (i.e., an X-ray generation area) of the target 9c in an area further toward the electron source 3 than the target 9c. If the electron path formation member 7 is made of a material which is capable of shielding the X-ray, most of the X-ray emitted toward the electron source 3 (i.e., a rear side) from the target 9c is shielded by an inner wall of the electron path 8 (i.e., the electron path formation member 7 surrounding the periphery of the electron path 8). The electron path formation member 7 forms a cylindrical-shaped X-ray path on the side further toward the X-ray extraction window 17 than the target 9c. If the electron path formation member 7 is made of a material which is capable of shielding the X-ray, an unnecessary X-ray among the X-ray emitted toward the X-ray extraction window 17 (i.e., a front side) from the target 9c is shielded by the inner wall of the X-ray path. The shape of the electron path 8 when seen from the electron source 3 may be suitably selected from among, for example, circular, rectangular or elliptical. Although the details will be described later, the electron path formation member 7 further has a function to generate an X-ray when the electrons which collide with the target 9c are reflected and then collide with the inner wall surface of the electron path 8. The electron path formation member 7 is in contact with the insulation oil 14. Therefore, the electron path formation member 7 further has a function to transfer heat generated in the target 9c to the insulation oil 14 and to make the heat escape out of the X-ray source 1.

It is desirable that the electron path formation member 7 is made by a material that is capable of shielding the X-ray generated at 30 kV to 150 kV. For example, besides tungsten and tantalum, molybdenum, zirconium and niobium and alloys thereof may be used. The electron path formation member 7 may be made of a material which generates an X-ray when electrons collide therewith. Alternatively, the electron path formation member 7 may be made of a material which does not generate an X-ray when electrons collide therewith. In this configuration, a material which generates an X-ray when electrons collide therewith is disposed at least a part of the inner wall surface of the electron path 8. It is desired that the electron path formation member 7 is made of the same material as that of the target 9c. It is desired that at least the material of the electron path formation member 7 which constitutes the inner wall surface of the electron path 8 is made of the same material as that of the target 9c. This is because the X-ray generated when the electrons emitted from the electron emitting portion 2 directly collide with the target 9c and the X-ray generated when the electrons reflected from the target 9c collide with the inner wall surface of the electron path 8 have the same characteristics.

The electron path formation member 7 and the target area 9 may be bonded by, for example, soldering. It is important in soldering that a vacuum state is kept inside the vacuum vessel 6. The material for soldering may be selected suitably depending on, for example, the material of the electron path formation member 7 or heatproof temperature of the electron path formation member 7.

The vacuum vessel 6 may be made of glass, ceramic, or other materials. Inside of the vacuum vessel 6 is formed as an evacuated (decompressed) internal space 13. It is only necessary that the degree of vacuum in the internal space 13 is determined such that electrons may fly across the distance between the electron source 3 and the target 9c which emits an X-ray, i.e., an electronic mean free path: for example, the degree of vacuum may be $1 \times 10^{-4}$ Pa or less. The degree of vacuum may be suitably determined depending on the electron source used and operating temperature. If, for example, a cold cathode electron source is used, the degree of vacuum is desirably $1 \times 10^{-6}$ Pa or less. It is also possible to provide the getter 12 in the internal space 13 or in an unillustrated auxiliary space which communicates with the internal space 13 for the purpose of keeping the degree of vacuum.

Hereinafter, a configuration of the anode 10 will be described in detail with reference to FIG. 1B. The anode 10 consists of the target area 9 and the electron path formation member 7. The target area 9 is configured such that the conductive layer 9b is provided on the substrate 9a and that the target 9c is provided at the central area on the conductive layer 9b as illustrated in FIG. 1B. In FIGS. 1B and 1C, d1 represents the diameter of the target 9c and d2 represents the inner diameter of the electron path 8. The target area 9 and the electron path formation member 7 are soldered to each other by unillustrated soldering material and therefore inside of the vacuum vessel 6 is kept in a vacuum state. The substrate 9a and the conductive layer 9b are also soldered to the electron path formation member 7. The conductive layer 9b in an area outside a dashed line in FIG. 1C is covered with the electron path formation member 7 when the target area 9 and the electron path formation member 7 are joined to each other.

An electron beam 5a generated by the electron source 3 collides with the target 9c via the electron path 8 constituted by the electron path formation member 7, and an X-ray 11a is generated at the target 9c. A part of the X-ray 11a is attenuated by self-absorption of the target 9c and also by the substrate 9a which functions also as the X-ray transmission window. However, the degree of such attenuation is small and therefore is tolerated substantially. Desirably, the diameter d1 of the target 9c is substantially the same as that of a cross section of the electron beam 5a. If there is a slight difference in diameter, the effect is limited but essentially not changed.

A part of electrons of the electron beam 5a which collide with the target 9c is reflected, and collides with the inner wall surface of the electron path 8 as reflected electrons 5b, at which an X-ray 11b (hereafter, "sub X-ray") is generated. The ratio of amount of the reflected electrons 5b among the electrons colliding with the target 9c is as large as about 50% depending on the material or surface conditions of the target 9c. Acceleration voltage at the time of collision of the reflected electrons 5b with the inner wall surface of the electron path 8 is lower than acceleration voltage of the electron beam 5a generated from the electron source 3. The degree varies depending, for example, on the material and surface conditions of the target 9c, and directions in which the electrons are reflected. Therefore, energy of the X-ray 11b is smaller than that of the X-ray 11a. The X-ray 11b is emitted in all the directions from the inner wall surface of the electron path 8 with which the reflected electrons 5b have collided. If the electron path formation member 7 is made of a material capable of shielding the X-ray, most part of the X-ray 11b emitted toward the rear side is shielded by the inner wall of the electron path 8. The X-ray 11b emitted toward the front side is made to transmit the target 9c and is emitted: therefore, the X-ray 11b may be taken out together with the X-ray 11a. A collimator for restricting the X-ray field may be provided outside the X-ray source 1.

A desirable range in which the inner wall surface of the electron path 8 becomes a sub X-ray generation potion will be described. The sub X-ray generating potion is disposed in a flat shape, and therefore will be referred to as "sub X-ray generation surface". Desirable ranges of the size of the opening 2R of the electron path formation member 7 (i.e., the diameter of the electron path 8) and the distance Z of the electron path 8 (i.e., the formation distance from the target 9c of the sub X-ray generation surface) will be described. A desirable range of the distance Z may be determined in consideration of density distribution of the reflected electrons having reached the periphery. With this reaching density distribution, many, i.e., about 80% of, reach points of electrons reflected off the target 9c exist on a peripheral surface of the electron path of which distance (coordinate) z from the target 9c is 2R or less R. About 95% of reach points exist when the distance z is 4R or less. If the distance z is 20R, the reach density of the reflected electrons converges to about zero. Therefore, when the size of the opening of the electron path formation member 7 is set to 2R, it is desirable that the sub X-ray generation surface is formed in an area at which the distance (size) Z is at least 2R or less and preferably 4R or less. Desirably, regarding the relationship between the size 2R of the opening of the electron path formation member 7 and the distance Z of the electron path, the following relationship is satisfied: $2R \leq Z \leq 20R$. It is further desirable that the following relationship is satisfied: $4R \leq Z \leq 20R$. In the present embodiment, the distance Z is equal to the length of the inner wall of the electron path formation member 7.

It is necessary that the size of the opening of the electron path formation member 7 is determined such that at least the electron beam 5 may be placed therein. The size of the opening is not uniquely determined because a convergence state of the electron beam 5 varies depending on the types of the electron source 3 or the types of a focusing electrode. If the shape of the opening is circular, the diameter of the opening is desirably 0.5 mm to 5.0 mm. It is necessary that the distance Z of the electron path 8 is 1 mm or more in order to achieve the X-ray shielding effect. Therefore, the distance Z is desirably 1 mm to 25 mm.

When the X-ray 11b transmits the target area 9, a part of the X-ray 11b transmits two layers, i.e., the conductive layer 9b and the substrate 9a, and the other part of the X-ray 11b transmits three layers, i.e., the target 9c, the conductive layer 9b and the substrate 9a. The target 9c needs to be made of a material with which the electron beam 5a collides to efficiently generate an X-ray, and needs to have suitable thickness. Therefore, the target 9c needs to be optimized depending on use conditions. Since the electron beam 5a rarely collides with and generates an X-ray on the conductive layer 9b, it is only necessary to consider electrical conductivity and radiolucency, which are inherent characteristics, regarding the conductive layer 9b. The energy of the X-ray 11b is smaller than the energy of the X-ray 11a as described above. Therefore, if the conductive layer 9b and the target 9c are made of the same material and have the same thickness, absorption of X-ray is great and thus the X-ray 11b is not sufficiently taken out. From the viewpoint of radiolucency, it is desirable that no conductive layer 9b is provided. However, from the viewpoint of prevention of above-described charge-up, a thinnest possible conductive layer 9b is needed.

Desirable materials with high radiolucency that may be used for the conductive layer 9b are light elements, such as aluminum, titanium, silicon nitride, silicon and graphite. It is only necessary that the thickness of the conductive layer 9b in a case in which elements that are smaller in mass than the target 9c is determined to keep its electrical conductivity: the thickness may be about 0.1 nm or more to 1 µm or less depending on the material. The conductive layer 9b and the target 9c may be made of the same material. If the conductive layer 9b and the target 9c are made of the same material, it is only necessary that the conductive layer 9b is thin enough not to substantially disturb transmission of the X-ray. Metallic materials of atomic numbers of 26 or more may be used as the target 9c if the thickness thereof is sufficiently small and, therefore, X-ray transmittance is high. For example, in a case in which tungsten is used, if the thickness of the tungsten layer is about 0.1 nm or more to 0.2 µm or less, the tungsten layer only slightly shields the X-ray and therefore may be used in the same manner as light elements. In such a configuration, with respect to the X-ray generated when the electrons reflected off the target 9c enter the inner wall surface of the electron path 8 (i.e., sub X-ray), the transmittance at the central area of the substrate 9a covered with the target 9c is 30% to 70% as compared with the transmittance of the peripheral area of the substrate 9a which is not covered with the target 9c.

In the example of FIG. 1B, the conductive layer 9b is disposed on the substrate 9a and the target 9c is disposed on the conductive layer 9b: however, this configuration is not restrictive.

If the target area 9 is configured such that the target 9c is disposed on the conductive layer 9b, it is desirable that the thickness of the conductive layer 9b in the area covered with the target 9c is 0.1 nm or more to 0.1 µm or less. This is because, if the thickness is in the above-described range, favorable linearity and output stability during emission of the X-ray may be provided. Note that the thickness of the conductive layer 9b is not necessarily in the above-described range in the area not covered with the target 9c. If the conductive layer 9b and the target 9c are made of the same material, the thickness of the conductive layer 9b in the area covered with the target 9c is not necessarily in the above-described range.

If the target area 9 is configured such that the conductive layer 9b is disposed on the target 9c, it is desired that the thickness of the conductive layer 9b which covers the target 9c is 0.1 nm or more to 0.1 µm. If the conductive layer 9b has the above-described thickness, the X-ray amount generated when the electrons directly collide with the conductive layer 9b is within a tolerance range. The thickness of the conductive layer 9b in an area except for the area in which the target 9c is covered is not necessarily within the above-described range because electrons do not directly collide with the conductive layer 9b in that area. If the conductive layer 9b and the target 9c are made of the same material, thickness of the conductive layer 9b in an area in which the target 9c is covered is not necessarily within the above-described range.

Second Embodiment

Figure 2A:
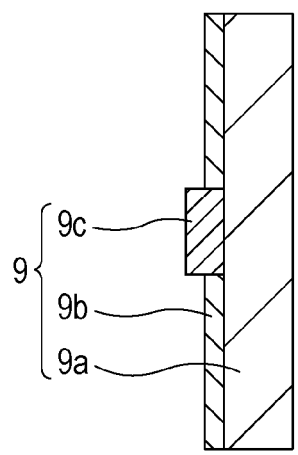
FIGS. 2A and 2B are schematic diagrams of another configuration of the target area according to a second embodiment of the present invention.
Figure 2B:
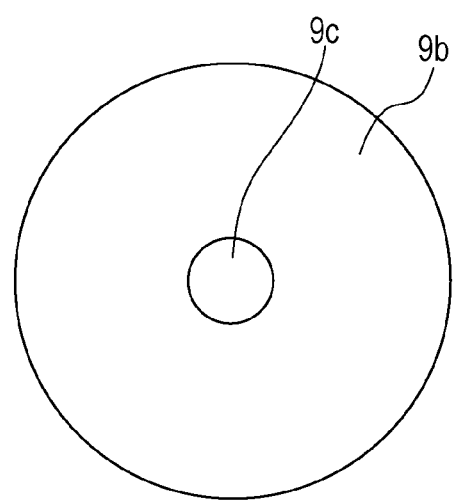

A second embodiment will be described with reference to FIGS. 2A and 2B. FIG. 2A is a cross-sectional view of a target area in the transmission type X-ray generator of the present embodiment. FIG. 2B is a plan view of a target area of FIG. 2A seen from the target side.

The X-ray generator of the present embodiment is provided with the same components as those of the first embodiment and has the same configuration as that of the first embodiment except for the target area 9. As illustrated in FIG. 2A, the target area 9 is configured such that the target 9c is disposed at the central area on the substrate 9a and that the conductive layer 9b is disposed on the substrate 9a in an area other than the central area. The target 9c is connected to the conductive layer 9b. Materials of the substrate 9a, the conductive layer 9b and the target 9c may be selected in the same manner as described in the first embodiment.

Third Embodiment

Figure 2C:
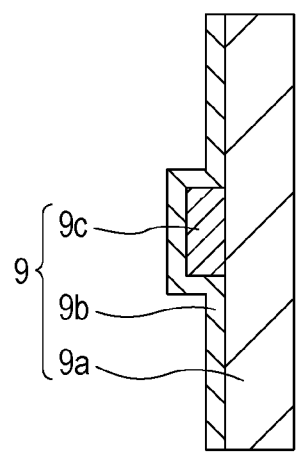
FIGS. 2C and 2D are schematic diagrams of another configuration of the target area according to a third embodiment of the present invention.
Figure 2D:
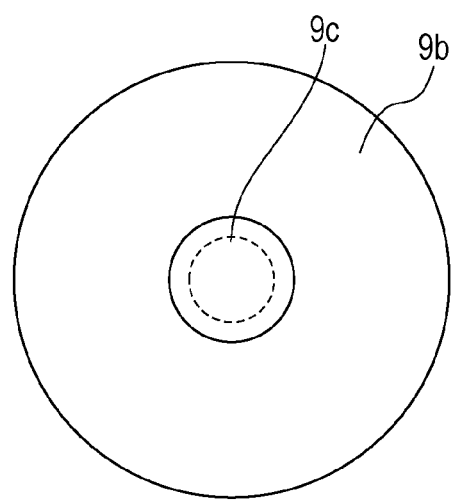

FIG. 2C is a cross-sectional view of a target area in the X-ray generator of the present embodiment. FIG. 2D is a plan view of the target area of FIG. 2C seen from the target side.

The X-ray generator of the present embodiment is provided with the same components as those of the first embodiment and has the same configuration as that of the first embodiment except for the target area 9. As illustrated in FIG. 2C, the target area 9 of the present embodiment is configured such that the target 9c is disposed at the central area on the substrate 9a, and that the conductive layer 9b is disposed on the substrate 9a in an area other than the central area and on the target 9c. The target 9c is covered with the conductive layer 9b. Materials of the substrate 9a, the conductive layer 9b and the target 9c may be selected in the same manner as described in the first embodiment.

Fourth Embodiment

Figure 3A:
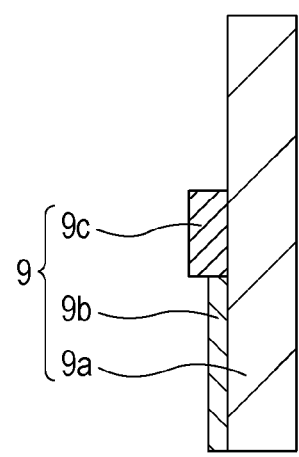
FIGS. 3A and 3B are schematic diagrams of another configuration of the target area according to a fourth embodiment of the present invention.
Figure 3B:
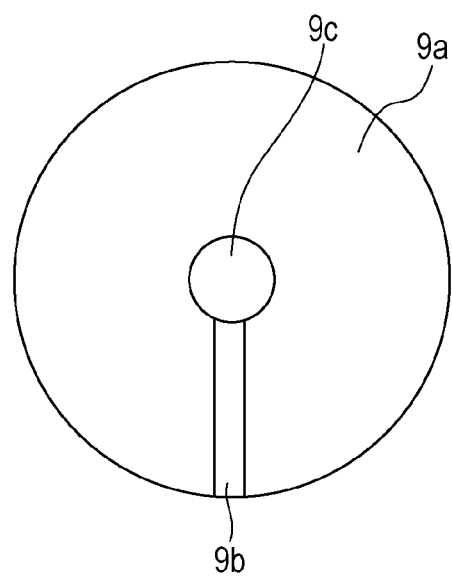

FIG. 3A is a cross-sectional view of a target area in the X-ray generator of the present embodiment. FIG. 3B is a plan view of the target area of FIG. 3A seen from the target side.

The X-ray generator of the present embodiment is provided with the same components as those of the first embodiment and has the same configuration as that of the first embodiment except for the target area 9. As illustrated in FIG. 3A, the target area 9 of the present embodiment is configured such that the target 9c is disposed at the central area on the substrate 9a, and that the conductive layer 9b extending toward a periphery of the target area 9 from the central area is disposed on the substrate 9a in a part of an area other than the central area. The target 9c is connected to the conductive layer 9b. In the peripheral area on the substrate 9a which is not covered with the target 9c, the conductive layer 9b is disposed at a part of this peripheral area and the rest of this peripheral area is a surface on which the substrate 9a is exposed. Materials of the substrate 9a, the conductive layer 9b and the target 9c may be selected in the same manner as described in the first embodiment.

Fifth Embodiment

Figure 3C:
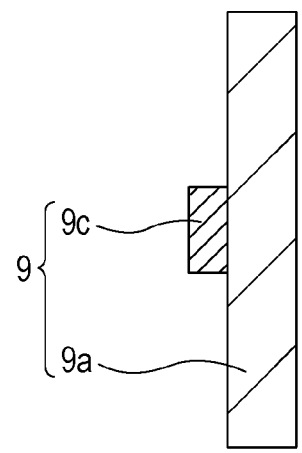
FIGS. 3C and 3D are schematic diagrams of another configuration of the target area according to a fifth embodiment of the present invention.
Figure 3D:
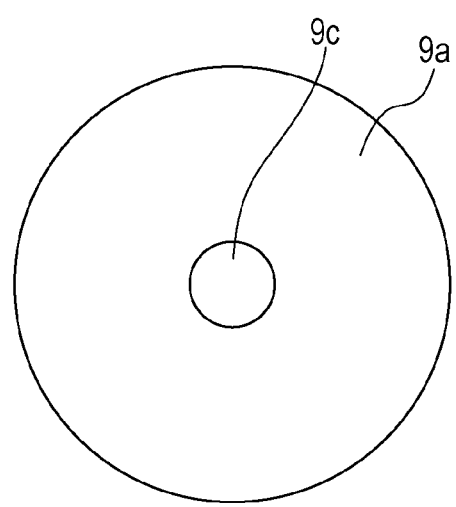

FIG. 3C is a cross-sectional view of a target area in the X-ray generator of the present embodiment. FIG. 3D is a plan view of the target area of FIG. 3C seen from the target side.

The X-ray generator of the present embodiment is provided with the same components as those of the first embodiment and has the same configuration as that of the first embodiment except for the target area 9. As illustrated in FIG. 3C, the target area 9 of the present embodiment is configured such that the target 9c is provided at the central area on the substrate 9a and that the conductive layer 9b is not provided. In this case, it is desirable that the substrate 9a has slight electrical conductivity. If electrical conductivity is insufficient, it is desirable to restrict, for example, use conditions so as not to cause charge-up. Materials of the substrate 9a and the target 9c may be selected in the same manner as described in the first embodiment.

Sixth Embodiment

Figure 4A:
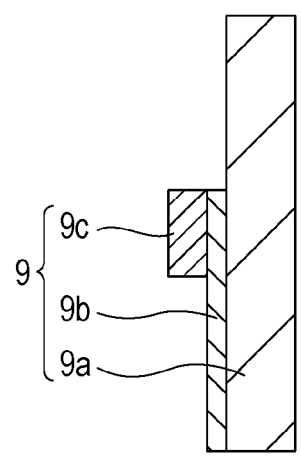
FIGS. 4A and 4B are schematic diagrams of another configuration of the target area according to a sixth embodiment of the present invention.
Figure 4B:
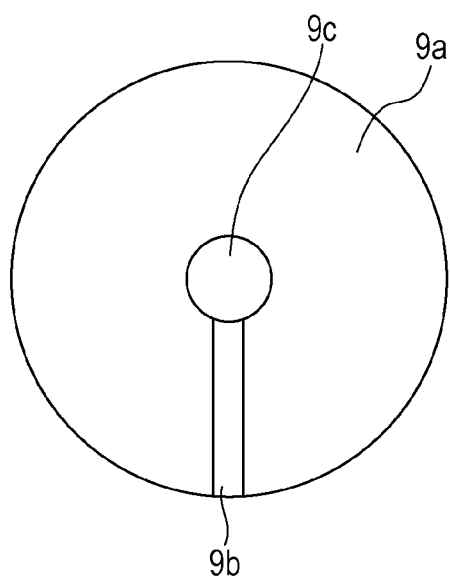

FIG. 4A is a cross-sectional view of a target area in the X-ray generator of the present embodiment. FIG. 4B is a plan view of the target area of FIG. 4A seen from the target side.

The X-ray generator of the present embodiment is provided with the same components as those of the first embodiment and has the same configuration as that of the first embodiment except for the target area 9. As illustrated in FIG. 4A, the target area 9 of the present embodiment is configured such that the conductive layer 9b is disposed at the central area on the substrate 9a, and that the conductive layer 9b extending toward the periphery of the substrate 9a from the central area is further disposed on the substrate 9a in a part of an area other than the central area. The target 9c is disposed on the conductive layer 9b situated at the central area on the substrate 9a. In the peripheral area on the substrate 9a which is not covered with the target 9c, the conductive layer 9b is disposed at a part of this peripheral area and the rest of this peripheral area is a surface on which the substrate 9a is exposed. Materials of the substrate 9a, the conductive layer 9b and the target 9c may be selected in the same manner as described in the first embodiment.

Seventh Embodiment

Figure 4C:
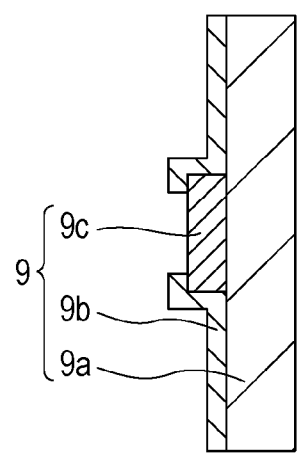
FIGS. 4C and 4D are schematic diagrams of another configuration of the target area according to a seventh embodiment of the present invention.
Figure 4D:
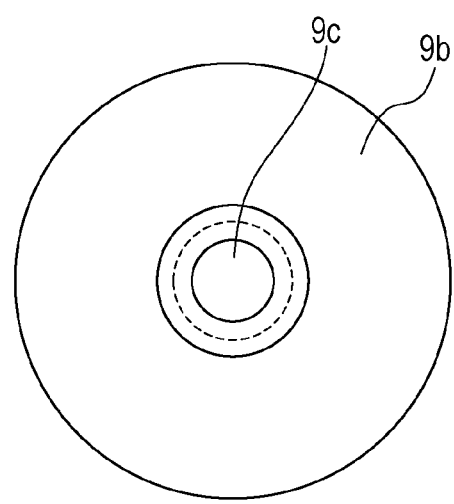

FIG. 4C is a cross-sectional view of a target area in the X-ray generator of the present embodiment. FIG. 4D is a plan view of the target area of FIG. 4C seen from the target side.

The X-ray generator of the present embodiment is provided with the same components as those of the first embodiment and has the same configuration as that of the first embodiment except for the target area 9. As illustrated in FIG. 3A, the target area 9 of the present embodiment is configured such that the target 9c is disposed at the central area on the substrate 9a, and that the conductive layer 9b is disposed on the substrate 9a in an area other than the central area and on a peripheral area of the target 9c. Materials of the substrate 9a, the conductive layer 9b and the target 9c may be selected in the same manner as described in the first embodiment.

Eighth Embodiment

Figure 4E:
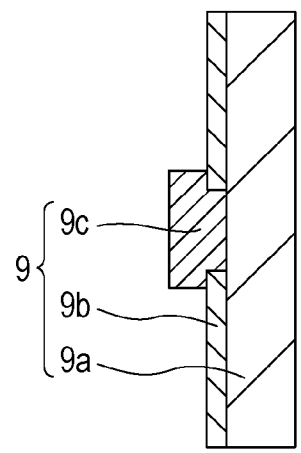
FIGS. 4E and 4F are schematic diagrams of another configuration of the target area according to an eighth embodiment of the present invention.
Figure 4F:
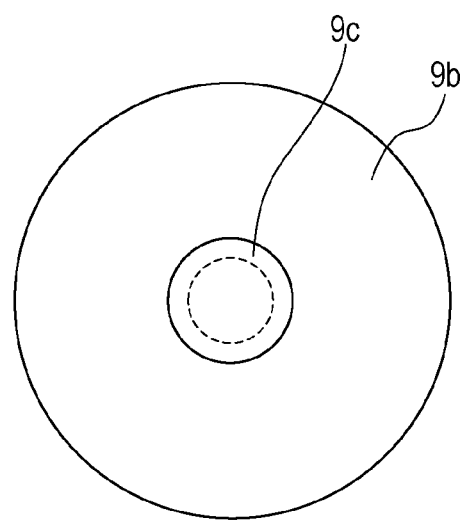

FIG. 4E is a cross-sectional view of the target area in the X-ray generator of the present embodiment. FIG. 4F is a plan view of the target area of FIG. 4E seen from the target side.

The X-ray generator of the present embodiment is provided with the same components as those of the first embodiment and has the same configuration as that of the first embodiment except for the target area 9. As illustrated in FIG. 4E, the target area 9 of the present embodiment is configured such that the conductive layer 9b is disposed on the substrate 9a in an area other than the central area, and that the target 9c is disposed on the substrate 9a in the central area and on the conductive layer 9b in a periphery of the central area. A part of the conductive layer 9b is covered with the target 9c. The substrate 9a, the conductive layer 9b and the target 9c may be made of the same materials as those in the first embodiment.

As described above, the sub X-ray may be generated at the inner wall surface of the electron path 8 by any of the embodiments described above. Since the peripheral area of the substrate 9a which is not covered with the target 9c is covered with the conductive layer 9b, transmittance of the sub X-ray in this peripheral area is higher than that of the central area. Therefore, besides the X-ray generated at the target 9c, the sub X-ray generated from the reflected electrons 5b generated at the target 9c may be taken out efficiently. In this manner, it is possible to improve X-ray generation efficiency.

Ninth Embodiment

Figure 5:
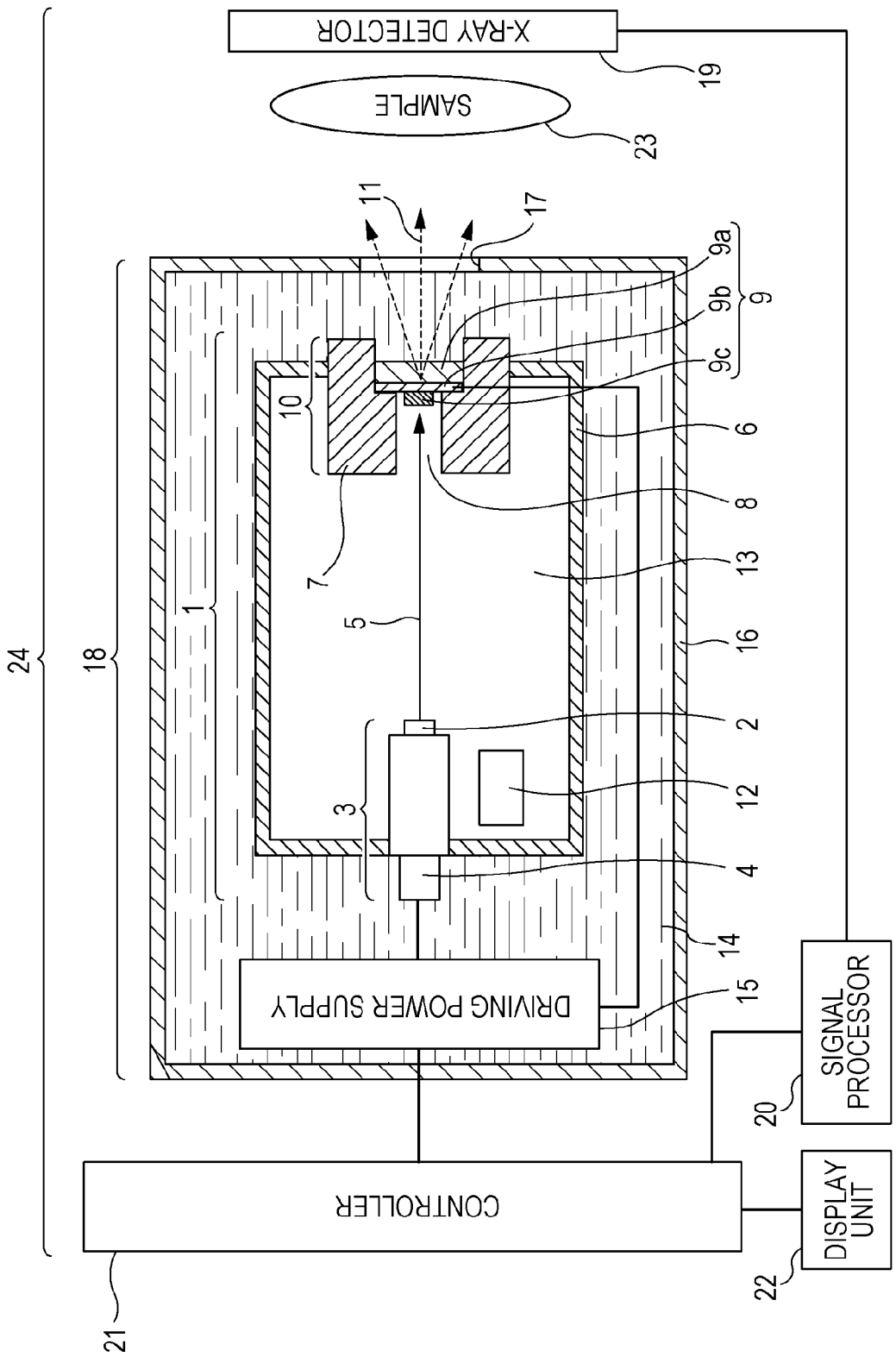
FIG. 5 is a configuration diagram of an X-ray imaging apparatus to which the transmission type X-ray generator according to the present invention is applied.

FIG. 5 is a schematic diagram of an X-ray imaging apparatus to which the X-ray generator of the ninth embodiment is applied. The X-ray imaging apparatus is provided with an X-ray generator 18, an X-ray detector 19, a signal processor 20, a device controller (hereafter, "controller") 21 and a display unit 22. The X-ray detector 19 is connected to the controller 21 via the signal processor 20. The controller 21 is connected to the display unit 22 and to the driving power source 15. As the X-ray generator 18, any of the transmission type X-ray generators of the first to eighth embodiments is suitable.

The controller 21 controls the X-ray generator 18 and the X-ray detector 19 in coordination with each other. The X-ray emitted from the X-ray generator 18 is detected by the X-ray detector 19 via a sample 23 and an X-ray transmission image of the sample 23 is captured. The captured X-ray transmission image is displayed on the display unit 22. For example, the controller 21 controls driving of the X-ray generator 18 and controls a voltage signal applied to the X-ray source 1 via the driving power source 15.

According to the present embodiment, since an X-ray generator with improved X-ray generation efficiency is applied, a compact and high-resolution X-ray imaging apparatus may be provided.

Hereinafter, the present invention will be described in detail with reference to Examples and Comparative Example.

Example 1

An X-ray generator of Example 1 is an X-ray generator provided with the target area 9 of FIG. 1B. The target area 9 illustrated in FIG. 1B is fabricated in the following manner: first, a 1-mm thick and 5-mm diameter single crystal diamond substrate is prepared as the substrate 9a and a titanium layer is formed to the thickness of 0.1 µm as the conductive layer 9b on the entire surface of the diamond substrate (i.e., a surface on which the electrons enter); and then a 1-mm diameter tungsten layer is formed, as a target 9c, to the thickness of 5 µm at the central area in which the titanium layer has been formed on the surface of the diamond substrate. Subsequently, the tungsten layer is used as the electron path formation member 7 and a 1.5-mm diameter electron path 8 is formed in the electron path formation member 7. Then, the substrate 9a and the conductive layer 9b are soldered to the electron path formation member 7, whereby the anode 10 illustrated in FIG. 1B is fabricated. The X-ray generator of FIG. 1A is fabricated using this anode 10.

Example 2

An X-ray generator of Example 2 is an X-ray generator provided with the target area 9 of FIG. 2A. The target area 9 illustrated in FIG. 2A is fabricated in the following manner: first, a 1-mm thick and 5-mm diameter single crystal diamond substrate is prepared as the substrate 9a; a 1-mm diameter tungsten layer as the target 9c is formed to the thickness of 5 µm at the central area of the surface of the diamond substrate; and then a titanium layer is formed to the thickness of 0.1 µm, as the conductive layer 9b, on the entire surface of the diamond substrate except for the area in which the tungsten layer has been formed. Then, the anode 10 is fabricated in the same manner as described in Example 1 and an X-ray generator to which the anode 10 is applied is fabricated in the same manner as described in Example 1.

Example 3

An X-ray generator of Example 3 is an X-ray generator provided with the target area 9 of FIG. 2C. The target area 9 illustrated in FIG. 2C is fabricated in the following manner: first, a 1-mm thick and 5-mm diameter single crystal diamond substrate is prepared as the substrate 9a; a 1-mm diameter tungsten layer as the target 9c is formed to the thickness of 5 µm at the central area of the surface of the diamond substrate; and then a titanium layer is formed to the thickness of 0.1 µm, as the conductive layer 9b, on the entire surface of the diamond substrate including the area in which the tungsten layer has been formed. Then, the anode 10 is fabricated in the same manner as described in Example 1 and an X-ray generator to which the anode 10 is applied is fabricated in the same manner as described in Example 1.

Example 4

An X-ray generator of Example 4 is an X-ray generator provided with the target area 9 of FIG. 2C. The X-ray generator of Example 4 differs from that of Example 3 in that tungsten is used as the conductive layer 9b. The target area 9 illustrated in FIG. 2C is fabricated in the following manner: first, a 1-mm thick and 5-mm diameter single crystal diamond substrate is prepared as the substrate 9a; a 1-mm diameter tungsten layer as the target 9c is formed to the thickness of 5 µm at the central area of the surface of the diamond substrate; and then a tungsten layer is formed to the thickness of 0.1 µm, as the conductive layer 9b, on the entire surface of the diamond substrate including the area in which the tungsten layer has been formed. Then, the anode 10 is fabricated in the same manner as described in Example 1 and an X-ray generator to which the anode 10 is applied is fabricated in the same manner as described in Example 1.

Example 5

An X-ray generator of Example 5 is an X-ray generator provided with the target area 9 of FIG. 3A. The target area 9 illustrated in FIG. 3A is fabricated in the following manner: first, a 1-mm thick and 5-mm diameter single crystal diamond substrate is prepared as the substrate 9a; a 1-mm diameter tungsten layer as the target 9c is formed to the thickness of 5 µm at the central area of the surface of the diamond substrate; and then a 0.3-mm wide and 0.1-µm thick titanium layer is formed to extend, in contact with the tungsten layer, to a periphery of the surface of the diamond substrate except for the area in which the tungsten layer has been formed. Then, the anode 10 is fabricated in the same manner as described in Example 1 and an X-ray generator to which the anode 10 is applied is fabricated in the same manner as described in Example 1.

Example 6

An X-ray generator of Example 6 is an X-ray generator provided with the target area 9 of FIG. 3C. The target area illustrated in FIG. 3C is fabricated in the following manner: first, a 1-mm thick and 5-mm diameter single crystal diamond substrate is prepared as the substrate 9a; and a 1-mm diameter tungsten layer as the target 9c is formed to the thickness of 5 µm at the central area of the surface of the diamond substrate. No conductive layer 9b is provided. Then, the anode 10 is fabricated in the same manner as described in Example 1 and an X-ray generator to which the anode 10 is applied is fabricated in the same manner as described in Example 1.

Comparison

As Comparative Example, an X-ray generator which includes a target area 9 in which a target 9c is disposed on an entire surface of a substrate 9a is fabricated. The target area 9 of Comparative Example is fabricated in the following manner: first, a 1-mm thick and 5-mm diameter single crystal diamond substrate is prepared as the substrate 9a; and a tungsten layer, as the target 9c, is formed to the thickness of 5 µm on the entire surface of the diamond substrate. Then, the anode 10 is fabricated in the same manner as described in Example 1 and an X-ray generator of Comparative Example to which the anode 10 is applied is fabricated in the same manner as described in Example 1.

Test Method

For the comparison, the amounts of X-rays obtained from the X-ray sources 1 of the X-ray generators fabricated in Examples and Comparison are measured using an X-ray measurement instrument of an ionization chamber system. Each X-ray source 1 is made to operate under the following conditions: the voltage applied to the X-ray source 1 is 60 kV and 100 kV, the current is 1 mA and the operating time is 0.1 seconds. The X-ray measurement instrument is located at a distance of 1 m from the position of the target area 9 and the X-ray amount is measured.

Measurement Result and Evaluation

In Examples and Comparison, measurement results of the amount of the X-ray obtained from the X-ray source 1 in accordance with the test method described above is illustrated in Table 1. In Table 1, the X-ray amounts in Examples 1 to 6 at 60 kV and 100 kV are represented by values on an index of 100, with 100 representing the X-ray amount of Comparison at 60 kV and 100 kV. The X-ray amount of Examples 1 to 6 at 60 kV is 114 to 118, and the X-ray amount of Examples 1 to 6 at 100 kV is 108 to 110. In each Example, a greater X-ray amount is obtained as compared with Comparison. It is considered that the reason why the X-ray amount obtained under voltage application 60 kV is greater than the case of 100 kV is, since X-ray energy is small, the X-ray amount to be absorbed is small by the configuration in which the layer in the area irradiated directly by the electron beam is omitted or thinned.

TABLE 1

|  | 60 kV | 100 kV |
| --- | --- | --- |
| EXAMPLE 1 | 115 | 108 |
| EXAMPLE 2 | 115 | 108 |
| EXAMPLE 3 | 116 | 109 |
| EXAMPLE 4 | 114 | 108 |
| EXAMPLE 5 | 118 | 110 |
| EXAMPLE 6 | 118 | 110 |
| COMPARISON | 100 | 100 |

While the present invention has been described with reference to exemplary embodiments and it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-189111, filed Aug. 31, 2011 which is hereby incorporated by reference herein in its entirety.

REFERENCE SIGNS LIST

1 X-ray source
7 electron passage formation member
8 electron passage
9 target area
9a substrate
9b conductive layer
9c target
18 transmission type X-ray generator

The invention claimed is:

1. A transmission type X-ray generator comprising:
an anode having an electron path formation member having an annular inner wall surface so as to define an electron path hole,
an integrated target including a target layer, an insulating substrate supporting the target layer and a conductive metal layer including a metal component, and
an electron source facing the target layer so as to irradiate the target layer with electrons passing through the electron path hole so as to generate a main X-ray,
wherein the electron path formation member has a sub X-ray generating portion receiving reflected electrons reflected from the target layer and generating a sub X-ray at the annular inner wall surface;
wherein the target layer is disposed at a central area of the insulating substrate and is remote from a periphery of the insulating substrate;
wherein the conductive metal layer is overlaid partially on the target layer such that the target layer is electrically connected to the electron path formation member via the conductive metal layer and the sub X-ray generating portion is irradiated with electrons reflected from the target layer or is overlaid under the target layer such that the target layer is electrically connected to the electron path formation member via the conductive metal layer and the sub X-ray generating portion is irradiated with electrons reflected from the target layer; and
wherein at least a part of a peripheral area of the integrated target corresponding to the substrate not covered with the target layer has higher transmittance than that of the central area of the integrated target corresponding to the substrate covered with the target layer, with respect to the sub X-ray.

2. The X-ray generator according to claim 1, wherein an X-ray transmittance of the integrated target corresponding to the central area of the substrate which is covered with the target layer is 30% to 70% of an X-ray transmittance at the peripheral area of the substrate which is not covered with the target layer.

3. The X-ray generator according to claim 1, further comprising:
an envelope in which the electron source and the target layer are stored,
wherein the electron path formation member and the target layer are disposed such that both the X-ray generated from the target layer which is directly irradiated with electrons and the X-ray generated from the annular inner wall surface of the electron path formation member which is irradiated with the electrons reflected from the target layer are made to emit outside from the envelope.

4. The X-ray generator according to claim 1, wherein a conductive metal layer connected to the target layer is provided in at least a part of a peripheral area of the substrate which is not covered with the target layer entirely.

5. The X-ray generator according to claim 4, wherein the thickness of the conductive metal layer is greater than that of the target layer.

6. The X-ray generator according to claim 4, wherein the conductive metal layer consists of elements which are smaller in mass than the target layer.

7. The X-ray generator according to claim 4, wherein the conductive metal layer is disposed in a part of a peripheral area of the substrate which is not covered with the target layer and the rest of the peripheral area of the substrate which is not covered with the target layer is a surface on which the substrate is exposed.

8. The X-ray generator according to claim 1, wherein at least a material of the electron path formation member which constitutes the annular inner wall surface of the electron path formation member is the same material as that of the target layer.

9. An X-ray imaging apparatus comprising:
an X-ray generator according to claim 1;
an X-ray detector which detects an X-ray emitted from the X-ray generator and transmitted through a sample; and
a controller which controls the X-ray generator and the X-ray detector in coordination with each other.

10. The X-ray generator according to claim 1, wherein the anode further comprises a conductive metal layer configured to be electrically connecting between the target layer and the electron path formation member.

* * * * *